United States Patent [19]

Sato et al.

[11] Patent Number: 5,151,547
[45] Date of Patent: Sep. 29, 1992

[54] PROCESS FOR PRODUCING ORGANIC CARBOXYLIC ACID ESTERS

[75] Inventors: Hiroshi Sato; Hiroshi Yoshioka, both of Ehime, Japan

[73] Assignee: Sumitomo Chemical Co., Ltd., Osaka, Japan

[21] Appl. No.: 664,198

[22] Filed: Mar. 4, 1991

[30] Foreign Application Priority Data

Mar. 5, 1990 [JP] Japan ................................ 2-54765
Oct. 11, 1990 [JP] Japan ................................ 2-274982

[51] Int. Cl.⁵ .............................................. C07C 69/52
[52] U.S. Cl. ................................. 560/205; 560/265
[58] Field of Search .............................. 560/205, 265

[56] References Cited

FOREIGN PATENT DOCUMENTS

| | | |
|---|---|---|
| 1468314 | 3/1969 | Fed. Rep. of Germany . |
| 425222 | 3/1942 | Japan . |
| 43-20286 | 8/1948 | Japan . |
| 42-6324 | 3/1967 | Japan . |
| 1017806 | 1/1966 | United Kingdom . |
| 1179356 | 1/1970 | United Kingdom . |
| 1422626 | 11/1973 | United Kingdom . |

*Primary Examiner*—Paul J. Killos
*Attorney, Agent, or Firm*—Sughrue, Mion, Zinn, Macpeak & Seas

[57] ABSTRACT

Disclosed is a process for producing an organic carboxylic acid ester from an organic carboxylic acid corresponding to said organic carboxylic acid ester and an alcohol by esterification reaction in gas phase which comprises carrying out the reaction with continuously or intermittently feeding sulfuric acid as a catalyst component in the presence of a catalyst carrier. The sulfuric acid may be previously supported on the catalyst carrier.

10 Claims, No Drawings

PROCESS FOR PRODUCING ORGANIC CARBOXYLIC ACID ESTERS

BACKGROUND OF THE INVENTION

1. Field of the Invention

The present invention relates to a process for producing organic carboxylic acid esters from the corresponding carboxylic acids and alcohols in a gas phase.

Not only are organic carboxylic acid esters useful compounds for coating compositions, adhesives, perfumes, plasticizers and solvents, but also, especially unsaturated carboxylic acid esters, are important intermediates as monomers or comonomers for various functional resins.

2. Description of the Related Art

The following processes have been known for producing organic carboxylic acid esters from the corresponding organic carboxylic acids and alcohols.

(1) Esterification in liquid phase using acid catalysts such as sulfuric acid, phosphoric acid, benzenesulfonic acid and p-toluenesulfonic acid.

(2) Continuous esterification in liquid phase using acidic cation exchange resins as catalysts.

(3) Esterification in gas phase using heteropoly-acid catalysts (Japanese Patent Kokai Nos. 57-99556 and 57-13095), composite oxide catalysts (Japanese Patent Kokoku Nos. 42-6324 and 45-24564 and Japanese Patent Kokai No. 51-75019), and catalysts comprising acids such as sulfuric acid, phosphoric acid, and benzenesulfonic acid supported on carriers (British Patent No. 1,017,806 and Japanese Patent Kokoku Nos. 42-5222 and 43-20286).

The process of carrying out esterification in liquid phase using acid catalysts such as sulfuric acid and phosphoric acid is generally carried out. However, since esterification of organic carboxylic acids is an equilibrium reaction, it is essential for increasing equilibrium conversion to remove and discharge the by-produced water from reaction system. Thus, the process suffer from many economical problems that alcohol must be used in excess amount, complicated means such as azeotropy with addition of other solvents are required and besides, corrosion of apparatuses is conspicuous.

The process of carrying out esterification in liquid phase using acidic cation exchange resins as catalysts has the merit that separation of reaction mixture and catalyst is easy and form of reaction is simplified, but has the economical disadvantages that cost of the resin is relatively high and reduction in activity due to deterioration of heat resistance and duration of life is unavoidable and regeneration or exchange at intervals is necessary.

Furthermore, when unsaturated carboxylic acids such as acrylic acid, methacrylic acid and crotonic acid are used as the organic carboxylic acids in these liquid phase processes, since starting materials and products are polymerizable, there occur troubles that efficient operation is hindered or recovery of product is lowered due to deposition of polymer in reaction apparatus or connecting lines.

The process of esterification in gas phase can solve the various problems in the process of esterification in liquid phase because the polymerization of unsaturated carboxylic acid does not substantially take place in gas phase state and furthermore, equilibrium shifts to the direction favorable for production system "AIChE Journal", 14(4), 606 ('68)].

However, there are still significant problems of insufficient activity and life of catalysts and the process has not yet been industrialized.

The object of the present invention is to provide an industrially advantageous process for producing organic carboxylic acid esters which is free from the above-mentioned defects in conventional processes.

The inventors have made intensive research in an attempt to find an excellent process for producing organic carboxylic acid esters in gas phase.

As a result, it has been found that reduction of activity of catalyst which supports sulfuric acid in esterification in gas phase is caused by desorption of the supported sulfuric acid and when sulfuric acid in an amount corresponding to the amount of sulfuric acid desorbed is continuously or intermittently supplied, no reduction of catalyst activity occurs and moreover, very high esterification activity can also be stably obtained by similarly supplying a catalytic amount of sulfuric acid in the presence of only carrier. Thus, the present invention has been accomplished.

SUMMARY OF THE INVENTION

That is, the present invention is a process for producing organic carboxylic acid esters from a corresponding organic carboxylic acids and alcohols in a gas phase, characterized in that reaction is carried out with continuous or intermittent supply of sulfuric acid as a catalyst component in the presence of a sulfuric acid-supported catalyst or a carrier.

DESCRIPTION OF THE PREFERRED EMBODIMENTS

Carriers used in the present invention include, for example, silica type carriers such as silica gel, diatomaceous earth, quartz sand, and quartz wool and inorganic compounds such as silicon carbide, silica-alumina, zeolite, titania, zirconia, alumina, active carbon and graphite.

Shape and particle size of carrier do not affect result of reaction, but the carrier may be molded into suitable shapes such as sphere and column.

The process of the present invention which comprises carrying out reaction while continuously or intermittently supplying sulfuric acid as catalyst in the presence of a carrier is effective regardless of the kind of carrier, but there are differences in the degree of esterification activity and sulfuric acid holding power (effect to inhibit desorption of sulfuric acid) depending on kind of carrier.

Of these carriers, silica type carriers such as silica gel, diatomeceous earth, quartz sand and quartz wool and silicon carbide are superior in sulfuric acid holding power and so sufficient reaction activity is exhibited even when amount of the continuously or intermittently supplied sulfuric acid is small and thus, these are preferred.

Furthermore, when catalysts comprising the above carriers on which sulfuric acid has been previously supported are used in the present invention, there is the advantage that the induction time before beginning of reaction can be shortened.

Sulfuric acid can be supported on carriers by known usual supporting methods, for example, evaporation method which comprises immersing a carrier in aqueous sulfuric acid solution and evaporating water with stirring to fix sulfuric acid on the carrier.

Supporting amount of sulfuric acid is not critical, but is usually about 1–50%, preferably about 5–20%.

Amount of sulfuric acid fed as a catalyst component together with starting materials of the reaction is usually about 1/20–1/10,000, preferably about 1/100–1/1,000 of the amount of organic carboxylic acid in molar ratio.

The sulfuric acid as catalyst component is fed continuously or intermittently, but may be fed singly or in admixture with one of starting materials of the reaction.

When sulfuric acid is fed intermittently, a given amount of sulfuric acid is periodically fed singly or in admixture with other starting material.

Catalyst activity and sulfuric acid-holding power vary depending on kind of carrier and hence, frequency of feeding and amount of sulfuric acid fed per one time differ depending on carrier used and are optionally determined considering catalyst activity in the reaction in the light of amount of sulfuric acid per organic carboxylic acid.

Organic carboxylic acids used in the present invention include, for example, saturated carboxylic acid such as formic acid, acetic acid, propionic acid, and butyric acid and unsaturated carboxylic acids such as acrylic acid, methacrylic acid and crotonic acid.

Alcohols used in the present invention are not critical and include, for example, aliphatic alcohols such as methanol, ethanol, n-propanol, isopropanol, n-butanol, sec-butanol, iso-butanol, tertbutanol and 2-ethyl-hexanol.

Molar ratio of alcohol/organic carboxylic acid is usually about 0.1/1–10/1, preferably about 0.5/1–5.0/1.

Purity of the starting materials is not especially needed to be high and esterification can be performed in the presence of a material which does not inhibit the reaction. For example, organic carboxylic acids are often produced by gas phase catalytic oxidation reaction of the corresponding organic aldehydes and dilute solution of organic carboxylic acid obtained by the oxidation reaction can be used as it is without concentration or purification of the solution. Alternatively, gaseous reaction mixture produced from the above gas phase oxidation process can be used directly as it is.

Reaction temperature is not critical, but is preferably a temperature at which starting materials can be kept in gaseous state, namely, about 100°–200° C. which may vary depending on organic carboxylic acid or alcohol used.

Reaction pressure can be widely chosen from reduced pressure to applied pressure and is not critical, but industrially about atmospheric pressure is preferred.

Contacting time of reaction gas and carrier (which is a value obtained by dividing volume of carrier by flow rate of reaction gas expressed by flow rate under standard temperature and pressure) is suitably about 1–70 seconds, preferably about 5–30 seconds.

The reaction is carried out using a gas phase flowing type reaction apparatus of fixed bed, fluidized bed, or moving bed type.

In the case of vertical gas phase reactor, there may be employed a method of charging starting materials from above and discharging reaction product from bottom or vice versa.

According to the present invention, since esterification activity is maintained by a slight amount of the fed sulfuric acid catalyst, deterioration of activity does not substantially occur and organic carboxylic acid esters can be produced selectively and in high yield for a long period of time.

Furthermore, polymerization of unsaturated carboxylic acid or produced unsaturated carboxylic acid ester in reaction system which is a problem in liquid phase esterification and corrosion of reaction apparatus in the case of using acid catalyst in liquid phase do not substantially occur in the gas phase esterification in the present invention and operation can be stably carried out for a long time.

The present invention will be explained in detail by the following nonlimiting examples.

Yield of ester is defined by the following formula.

$$\text{Yield} (\%) = \frac{\text{Mol number of carboxylic acid ester produced}}{\text{Mole number of carboxylic acid fed for reaction}} \times 100$$

Example 1

Three hundred ml of aqueous silica sol (SNOWTEX N; $SiO_2 = 20\%$, manufactured by Nissan Chemical Industries, Ltd.) was mixed with 9.6 ml of 96% sulfuric acid and the mixture was dried under reduced pressure at 120° C. for 3 hours by a rotary evaporator to prepare a silica gel catalyst supporting 20% sulfuric acid.

Six ml of the above catalyst (10–16 mesh) was packed in a pyrex glass reaction tube of 8 mm in inner diameter and production of ethyl acrylate from acrylic acid and ethanol was carried out therein using nitrogen gas as a carrier gas under the following conditions.

As catalyst, sulfuric acid in an amount corresponding to 1/670 (molar ratio) of feeding amount of acrylic acid was dissolved in ethanol and this solution was continuously fed.

Feed composition (mmol/hr): Acrylic acid/ethanol/$N_2$ = 16/32/27

Total feeding amount: 75 mmol/hr

SV (space velocity) = 280 ml/ml-catalyst.hr

Contacting time: 12.9 seconds

Reaction temperature (furnace temperature) = 145° C.

The product was trapped at 0° C. and the trapped liquid was analyzed by gas chromatography.

Reaction elapsed time and results of reaction are shown in Table 1. The results of reaction are shown based on acrylic acid.

TABLE 1

| Reaction elapsed time | Yield of EA *1 (%) | STY of EA *2 |
|---|---|---|
| 7 hr | 91.1 | 0.243 |
| 23 hr | 92.0 | 0.245 |
| 101 hr | 93.6 | 0.250 |
| 146 hr | 92.9 | 0.248 |

*1 EA: Ethyl acrylate
*2 STY: Space time yield (kg-EA/l-carrier · hr)

Comparative Example 1

Ethyl acrylate was produced from acrylic acid and ethanol in the same manner as in Example 1 except that sulfuric acid as catalyst was not dissolved in ethanol, namely, continuous feeding of sulfuric acid was not carried out.

Reaction elapsed time and results of the reaction are shown in Table 2.

TABLE 2

| Reaction elapsed time | Yield of EA *1 (%) | STY of EA *2 |
|---|---|---|
| 5 hr | 93.0 | 0.248 |
| 20 hr | 91.8 | 0.245 |
| 48 hr | 88.9 | 0.237 |
| 97 hr | 52.2 | 0.139 |

*1 EA: Ethyl acrylate
*2 STY: Space time yield (kg-Ea/l-carrier · hr)

Example 2

Six ml of 20% sulfuric acid supporting silica gel catalyst (10-16 mesh) prepared in Example 1 was packed in a pyrex glass fixed bed type gas phase flowing reaction apparatus and n-butyl acrylate was produced from acrylic acid and n-butanol using nitrogen gas as a carrier gas under the following conditions.

As catalyst, sulfuric acid in an amount corresponding to 1/670 (molar ratio) of feeding amount of acrylic acid was dissolved in n-butanol and this solution was continuously fed.

Feed composition (mmol/hr): Acrylic acid/n-butanol/$N_2$ = 16/32/54
Total feeding amount: 102 mmol/hr
SV (space velocity) = 380 ml/ml-catalyst.hr
Contacting time: 9.5 seconds
Reaction temperature (furnace temperature) = 145° C.

The product was trapped at 0° C. and the trapped liquid was analyzed by gas chromatography.

Reaction elapsed time and results of reaction are shown in Table 3. The results of reaction are shown based on acrylic acid.

TABLE 3

| Reaction elapsed time | Yield of BA *1 (%) | STY of BA *2 |
|---|---|---|
| 6 hr | 86.9 | 0.297 |
| 78 hr | 91.6 | 0.313 |
| 148 hr | 90.3 | 0.308 |
| 237 hr | 91.1 | 0.311 |

*1 BA: n-butyl acrylate
*2 STY: Space time yield (kg-BA/l-carrier · hr)

Comparative Example 2

N-butyl acrylate was produced from acrylic acid and n-butanol in the same manner as in Example 2 except that sulfuric acid as catalyst was not dissolved in n-butanol, namely, continuous feeding of sulfuric acid was not carried out.

Reaction elapsed time and results of the reaction are shown in Table 4.

TABLE 4

| Reaction elapsed time | Yield of BA *1 (%) | STY of BA *2 |
|---|---|---|
| 2 hr | 94.9 | 0.324 |
| 18 hr | 98.6 | 0.337 |
| 48 hr | 97.3 | 0.332 |
| 87 hr | 41.1 | 0.140 |

*1 BA: n-butyl acrylate
*2 STY: Space time yield (kg-BA/l-carrier · hr)

Example 3

Three hundred ml of aqueous silica sol (SNOWTEX N; $SiO_2$=20%, manufactured by Nissan Chemical Industries, Ltd.) was dried under reduced pressure at 120° C. for 3 hours in a rotary evaporator to prepare silica gel.

The resulting silica gel powder was tablet molded into columns of 5 mm in diameter and 5 mm in height, which were calcined at 1250° C. for 2 hours under flow of air to obtain carriers. Twenty ml of the carriers were packed in a pyrex glass reaction tube of 13 mm in inner diameter and production of methyl methacrylate from methacrylic acid and methanol was carried out using nitrogen gas as a carrier gas under the following conditions.

As catalyst, sulfuric acid in an amount corresponding to 1/670 (molar ratio) of feeding amount of methacrylic acid was dissolved in methanol and this solution was continuously fed.

Feed composition (mmol/hr): Methacrylic acid/methanol/$N_2$ = 48/96/30
Total feeding amount: 174 mmol/hr
SV (space velocity) = 195 ml/ml-catalyst.hr
Contacting time: 18.5 seconds
Reaction temperature (furnace temperature) = 160° C.

The product was trapped at 0° C. and the trapped liquid was analyzed by gas chromatography.

Reaction elapsed time and results of reaction are shown in Table 5. The results of reaction are shown based on methacrylic acid.

TABLE 5

| Reaction elapsed time | Yield of MMA *1 (%) | STY of MMA *2 |
|---|---|---|
| 1 day | 25.1 | 0.060 |
| 2 days | 85.0 | 0.204 |
| 3 days | 96.2 | 0.231 |
| 10 days | 98.9 | 0.237 |
| 20 days | 98.0 | 0.235 |
| 30 days | 98.1 | 0.235 |

*1 MMA: Methyl methacrylate
*2 STY: Space time yield (kg-MMA/l-carrier · hr)

Example 4

Three hundred ml of aqueous silica gel (SNOWTEX N; $SiO_2$=20%, manufactured by Nissan Chemical Industries, Ltd.) was mixed with 2.0 cc of 96% sulfuric acid and the mixture was dried under reduced pressure at 90° C. for 2 hours by a rotary evaporator to prepare a 5% sulfuric acid supporting silica gel catalyst.

Twelve ml of the above catalyst (10-16 mesh) was packed in a pyrex glass reaction tube of 8 mm in inner diameter and production of ethyl acetate from acetic acid and ethanol was carried out using nitrogen gas as a carrier gas under the following conditions.

As catalyst, sulfuric acid in an amount corresponding to 1/820 (molar ratio) of feeding amount of acetic acid was dissolved in ethanol and this solution was continuously fed.

Feed composition (mmol/hr): Acetic acid/ethanol/$N_2$ = 25/50/32
Total feeding amount: 107 mmol/hr
SV (space velocity) = 200 ml/ml-catalyst.hr
Contacting time: 18.0 seconds
Reaction temperature (furnace temperature) = 140° C.

The product was trapped at 0° C. and the trapped liquid was analyzed by gas chromatography.

Reaction elapsed time and results of reaction are shown in Table 6. The results of reaction are shown based on acetic acid.

TABLE 6

| Reaction elapsed time | Yield of ethyl acetate (%) | STY of ethyl acetate *1 |
|---|---|---|
| 4 hr | 85.1 | 0.156 |
| 119 hr | 75.6 | 0.139 |
| 148 hr | 70.3 | 0.129 |
| 172 hr | 71.6 | 0.131 |

*1 STY: Space time yield (kg-ethyl acetate/l-carrier · hr)

Comparative Example 3

Ethyl acetate was produced from acetic acid and ethanol in the same manner as in Example 4 except that sulfuric acid as catalyst was not dissolved in ethanol, namely, continuous feeding of sulfuric acid was not carried out. Reaction elapsed time and results of the reaction are shown in Table 7.

TABLE 7

| Reaction elapsed time | Yield of ethyl acetate (%) | STY of ethyl acetate *1 |
|---|---|---|
| 1 hr | 83.0 | 0.152 |
| 20 hr | 16.0 | 0.029 |
| 43 hr | 12.0 | 0.022 |

*1 STY: Space time yield (kg-ethyl acetate/l-carrier · hr)

We claim:

1. A process for producing an organic carboxylic acid ester from an organic carboxylic acid selected from the group consisting of formic acid, acetic acid, propionic acid, butyric acid, acrylic acid, methacrylic acid and crotonic acid corresponding to said organic carboxylic acid ester and an alcohol selected from the group consisting of methanol, ethanol, n-propanol, isopropanol, n-butanol, sec-butanol, iso-butanol, tert-butanol and 2-ethyl-hexanol by esterification reaction in gas phase which comprises carrying out the reaction with continuously or intermittently feeding sulfuric acid as a catalyst component in the presence of a catalyst carrier.

2. A process according to claim 1, wherein sulfuric acid is previously supported on the catalyst carrier.

3. A process according to claim 2, wherein amount of sulfuric acid supported on the carrier is about 1–50%.

4. A process according to claim 1 or 2, wherein the catalyst carrier is silicon carbide or at least one silica selected from the group consisting of silica gel, diatomaceous earth, quartz sand and quartz wool.

5. A process according to claim 1 or 2, wherein amount of sulfuric acid fed is about 1/20–1/10,000 of that of the organic carboxylic acid in molar ratio.

6. A process according to claim 1 or 2, wherein molar ratio of alcohol/organic carboxylic acid is about 0.1/1–10/1.

7. A process according to claim 1 or 2, wherein reaction temperature is about 100°–200° C.

8. A process according to claim 1 or 2, wherein contacting time of reaction gas with the catalyst carrier is about 1–70 seconds.

9. A process according to claim 1 or 2, wherein the organic carboxylic acid is acrylic acid or methacrylic acid.

10. A process according to claim 1 or 2, wherein the alcohol is methanol, ethanol, propanol, butanol or 2-ethyl-hexanol.

* * * * *